(12) United States Patent
Belgrader

(10) Patent No.: US 8,236,501 B2
(45) Date of Patent: Aug. 7, 2012

(54) APPARATUS, SYSTEM AND METHOD FOR PURIFYING NUCLEIC ACIDS

(75) Inventor: Phillip Belgrader, Serverna Park, MD (US)

(73) Assignee: Akonni Biosystems, Inc., Frederick, MD (US)

( * ) Notice: Subject to any disclaimer, the term of this patent is extended or adjusted under 35 U.S.C. 154(b) by 212 days.

(21) Appl. No.: 12/793,218

(22) Filed: Jun. 3, 2010

(65) Prior Publication Data

US 2010/0240882 A1   Sep. 23, 2010

Related U.S. Application Data

(62) Division of application No. 11/933,113, filed on Oct. 31, 2007, now Pat. No. 7,759,112.

(51) Int. Cl.
*C12M 1/00* (2006.01)
*C12M 3/00* (2006.01)
*B01D 21/00* (2006.01)
*C07H 21/04* (2006.01)

(52) U.S. Cl. .................. 435/6.1; 435/283.1; 435/287.7; 435/288.6; 422/527; 422/534; 422/535; 536/23.1

(58) Field of Classification Search .................. None
See application file for complete search history.

(56) References Cited

U.S. PATENT DOCUMENTS

| | | | |
|---|---|---|---|
| 4,475,821 A | 10/1984 | Koch et al. | |
| 4,765,818 A | 8/1988 | Che et al. | |
| 4,810,674 A | 3/1989 | Che et al. | |
| 4,999,164 A | 3/1991 | Puchinger et al. | |
| 5,496,523 A | 3/1996 | Gazit et al. | |
| 5,833,927 A | 11/1998 | Raybuck et al. | |
| 5,876,918 A | 3/1999 | Wainwright et al. | |
| 6,048,457 A | 4/2000 | Kopaciewicz et al. | |
| 6,074,827 A | 6/2000 | Nelson et al. | |
| 6,084,091 A | 7/2000 | Muller et al. | |
| 6,200,474 B1 | 3/2001 | Kopaciewicz et al. | |
| 6,274,371 B1 | 8/2001 | Colpan | |
| 6,337,214 B1 | 1/2002 | Chen | |
| 6,537,502 B1 | 3/2003 | Shukla et al. | |
| 6,958,392 B2 | 10/2005 | Fomovskaia et al. | |
| 7,615,347 B2 * | 11/2009 | Fukasawa et al. | ............ 435/6.12 |
| 2004/0054160 A1 | 3/2004 | Pal | |
| 2004/0122222 A1 | 6/2004 | Sakura et al. | |
| 2005/0092685 A1 | 5/2005 | Hilhorst et al. | |
| 2006/0124551 A1 | 6/2006 | Gjerde et al. | |

(Continued)

FOREIGN PATENT DOCUMENTS

WO    WO 00/21973    *    4/2000

(Continued)

OTHER PUBLICATIONS

Whatman catalog website "Glass Microfiber Filters" 2007-2009.*

(Continued)

*Primary Examiner* — Betty Forman
(74) *Attorney, Agent, or Firm* — Andrews Kurth, LLP; Michael Ye

(57) ABSTRACT

Methods and devices for isolating nucleic acids from a mixture containing such nucleic acids and extraneous matter are provided. In one embodiment, the method of the invention comprises passing the mixture through a glass frit under conditions effective to separate the nucleic acids from the extraneous matter. In a more specific embodiment, the glass frit is a sintered glass fit.

16 Claims, 8 Drawing Sheets

U.S. PATENT DOCUMENTS

2006/0160064 A1     7/2006    Carbonell
2008/0234474 A1*   9/2008    Braman et al. ............... 536/25.3

FOREIGN PATENT DOCUMENTS

WO    PCT/US08/056482     3/2008
WO    PCT/US08/068159     6/2008

OTHER PUBLICATIONS

Whatman catalog website "Glass Microfiber Binder Free" downloaded Mar. 2010: pp. 1-2 of 6.*

Chandler, Darrell P., et al, Renewable Microcolumns for Solid-Phase Nucleic Acid Separations and Analysis . . . ; Trends in Analytical Chemistry; vol. 19. No. 5; 2000; pp. 314-321.

Niederkofler, Eric E., Novel Mass Spectrometric Immunoassays for the Rapid Structural Characterization of Plasma Apolipo..; Journal of Lipid Research; vol. 44; 2003; pp. 630-639.

Written Opinion, Aug. 25, 2008.

Written Opinion, Jan. 9, 2009.

Search Report, Jan. 22, 2009.

* cited by examiner

APPARATUS, SYSTEM AND METHOD FOR PURIFYING NUCLEIC ACIDS

RELATED APPLICATION

This Application is a Divisional Application of U.S. patent application Ser. No. 11/933,113, filed on Oct. 31, 2007.

1 BACKGROUND OF THE INVENTION

1.1 Field of the Invention

This invention relates to the purification of chemical substances, and, more particularly, to devices, methods, and systems for performing chemical purification and analysis. More particularly, the devices, methods, and systems provided by the invention have particularly useful application in the purification and analysis of nucleic acids, and, more particularly to microfluidic devices for performing such purification and analysis. The invention has applications in the areas of analytical chemistry, forensic chemistry, microfluidics and microscale devices, medicine, and public health.

1.2 The Related Art

The extension of semiconductor fabrication techniques to create highly miniaturized chemical devices (Beach, Strittmatter et al. 2007) has created a revolution in analytical chemistry, especially by providing a means for identifying chemical substances present in minute concentrations in complex mixtures with great precision and accuracy. This revolution has had noticeable impact in chemical processing, medicine, forensic science, and national defense, where such devices provide fast, portable, and economic biological detectors. Examples of such devices include devices for collecting and identifying particulates (Wick 2007), systems for detecting molecular contaminants (Knollenberg, Rodier et al. 2007), and devices for detecting proteins (Terry, Scudder et al. 2004; Deshmukh 2006). Other devices use fluidic technologies to isolate and/or amplify nucleic acids using Polymerase Chain Reaction (PCR) in an automated system. Examples of such devices are those sold commercially by Qiagen (Hilden, Germany), Roche (Basel, Switzerland), Applied Biosystems (Foster City, Calif.), Idaho Technologies (Salt Lake City, Utah), and Cepheid (Sunnyvale, Calif.).

But as with any analytical process, preparing the sample prior to processing is critical to good performance. The presence of too many complicating factors and concentrations of substances that may mask analytes of interest can render robust detection all but impossible. This problem is of particular concern when attempting to analyze the nucleic acid content of cell lysates, which are extremely complex and heterogenous mixtures (Colpan 2001). The preparatory task is made still more difficult where portable analytical devices are concerned, since those devices are expected to be used in locations where common laboratory support equipment, such as centrifuges and separation columns, are not available. In those cases, some means for filtering a raw sample, such as a blood or urine sample, is critical to providing meaningful results. Current devices based on fluidic technologies, in particular the above-mentioned Qiagen devices, use glass filters that are soft and compliant, requiring a support matrix. The filters have small pore sires, typically between about one- and three microns, to get efficient capture of the nucleic acids from the sample. Because of the small pores sires, the filters are also relatively thin, typically less than two millimeters thick to reduce fluid flow resistance when sample is forced though the small pore sires. In the Qiagen procedure, typically a sample is mixed with a chaotropic agent, such as guanidine, and the mixture is passed through the glass filter using centrifugal force, in which fluid flows in only one direction. Nucleic acids bind to the glass filter; they are washed with ethanol or isopropanol, and subsequently released using a ten millimolar (10 mM) Tris buffer at a pH of about eight (pH 8.0) or water. But the small pore sizes limit the amount of sample that can be processed, due to resistance created by fluid flow and potential for clogging created by greater flow rates. Thus, devices such as the Qiagen devices can be easily damaged or otherwise rendered ineffective easily. Moreover, these characteristics limit sample input volume, the types of samples that can be examined, large-volume samples, concentration factors, and simple fluidic integration.

Larger glass filters have been used to provide pre-processing filtration of samples. For example, U.S. Pat. No. 4,912,034 (Kalra, Pawlak et al. 1990) describes an immunoassay for detecting a target analyte in a liquid sample that includes an optional prefilter assembly made of glass fibers. However, this device is not a microfluidic device and does not show or suggest the use of glass fits as a filter prior to microscale PCR reactions. U.S. Pat. No. 4,923,978 (McCormack 1990) describes prior uses of glass fiber filters to remove unwanted protein- and protein-DNA complexes from aqueous DNA samples, but in a disparaging manner noting that such filters have low binding capacities (see Column 2). Indeed, the '978 patent claims a very different material for performing such filtrations. U.S. Pat. No. 6,274,371 (Colpan 2001) describes silica gel, aluminum oxide, and diatomaceous earth as a preferred filtering agent for removing unwanted contaminants from cellular lysates prior to nucleic acid analysis. U.S. Pat. No. 6,800,752 (Tittgen 2004) describes using a chromatography material to separate mixtures comprising nucleic acids, in which the material includes carrier and ion exchanger functions wherein the carrier comprises a fibrous material on a support, such as a plastic frit.

Nevertheless, there remains therefore a need to provide fluidic devices that are effective to isolate and identify nucleic acids that overcome the limitations of the current generation of such devices. The present invention meets these and other needs.

2 SUMMARY OF THE INVENTION

In a first aspect, the present invention provides a method for isolating nucleic acids from a mixture containing such nucleic acids and extraneous matter. Suitable nucleic acids for use in the present invention include microbial DNA and human genomic DNA. In one embodiment, the method of the invention comprises passing the mixture through a glass frit under conditions effective to separate the nucleic acids from the extraneous matter. In a more specific embodiment, the glass fit is a sintered glass frit. In some embodiments, the glass frit has a pore size between about 2 microns and about 220 microns; in more specific embodiments, the glass frit has a pore size between about 150 microns and about 200 microns; in other more specific embodiments, the glass fit has a pore size between about 2 microns and about 100 microns; and still more specifically, the glass frit has a pore size between about 40 microns and about 75 microns; yet other more specific embodiments includes those in which the glass frit has a pore size between about 2 microns and about 20 microns. In another embodiment, the method of the invention includes passing the mixture through a glass frit to produce thereby a first-filtered mixture and then passing the first-filtered mixture through a second glass frit under conditions effective to separate the nucleic acids from the first-filtered mixture.

In a second aspect, the present invention provides a device for filtering isolating nucleic acids from a mixture containing such nucleic acids and extraneous matter. In some embodiments, the device comprises a hollow chamber having an inlet and an outlet; and disposed therein at least one glass frit having a pore size of between about 2 microns and about 220 microns and arranged at a location intermediate the inlet and the outlet. In more specific embodiments, the glass frit is a sintered glass frit. In other embodiments, the glass frit is a sintered glass frit. In some embodiments, the glass frit has a pore size between about 2 microns and about 220 microns; in more specific embodiments, the glass frit has a pore size between about 150 microns and about 200 microns; in other more specific embodiments, the glass frit has a pore size between about 2 microns and about 100 microns; and still more specifically, the glass frit has a pore size between about 40 microns and about 75 microns; yet other more specific embodiments includes those in which the glass frit has a pore size between about 2 microns and about 20 microns.

In a third aspect, the present invention provides a fluidic device for identifying one or more nucleic acids from a mixture of such nucleic acids and extraneous matter. In some embodiments, the fluid device of the invention comprises: an inlet, an outlet, and at least one fluidic reaction chamber intermediate the inlet and the outlet and in communication with each of the inlet and the outlet. The device further comprise at least one glass frit arranged at a location (or locations) proximal to the inlet and the reaction chamber(s) and in fluidic communication with each of the inlet and reaction chamber(s). The glass frit(s) have a pore size of between about 2 microns and about 220 microns. The mixture enters the device through the inlet and passes through the glass frit to exit therefrom as a filtered product before entering the fluidic reaction chamber(s). At least one fluidic reagent dispenser is arranged intermediate the glass frit and the reaction chamber(s) and in fluidic communication therewith. In a more specific embodiment, the glass frit is a sintered glass frit. In some embodiments, the glass frit has a pore size between about 2 microns and about 220 microns; in more specific embodiments, the glass frit has a pore size between about 150 microns and about 200 microns; in other more specific embodiments, the glass frit has a pore size between about 2 microns and about 100 microns; and still more specifically, the glass frit has a pore size between about 40 microns and about 75 microns; yet other more specific embodiments includes those in which the glass frit has a pore size between about 2 microns and about 20 microns. In another embodiment, the fluidic device includes a heater proximal to the glass frit(s).

These and other aspects and advantages will become apparent when the Description below is read in conjunction with the accompanying Drawings.

3 BRIEF DESCRIPTION OF THE DRAWINGS

FIG. 1 is a schematic illustration of a glass frit device ("a filter module") for purifying nucleic acids in accordance with the present invention.

FIGS. 2A and 2B are illustrations of a filter in accordance with the present invention. FIG. 2A is an illustration an exploded view of a glass frit device ("a filter module") for purifying nucleic acids in accordance with the present invention. FIG. 2B is a cut-away illustration of the same device.

Figure 2A:
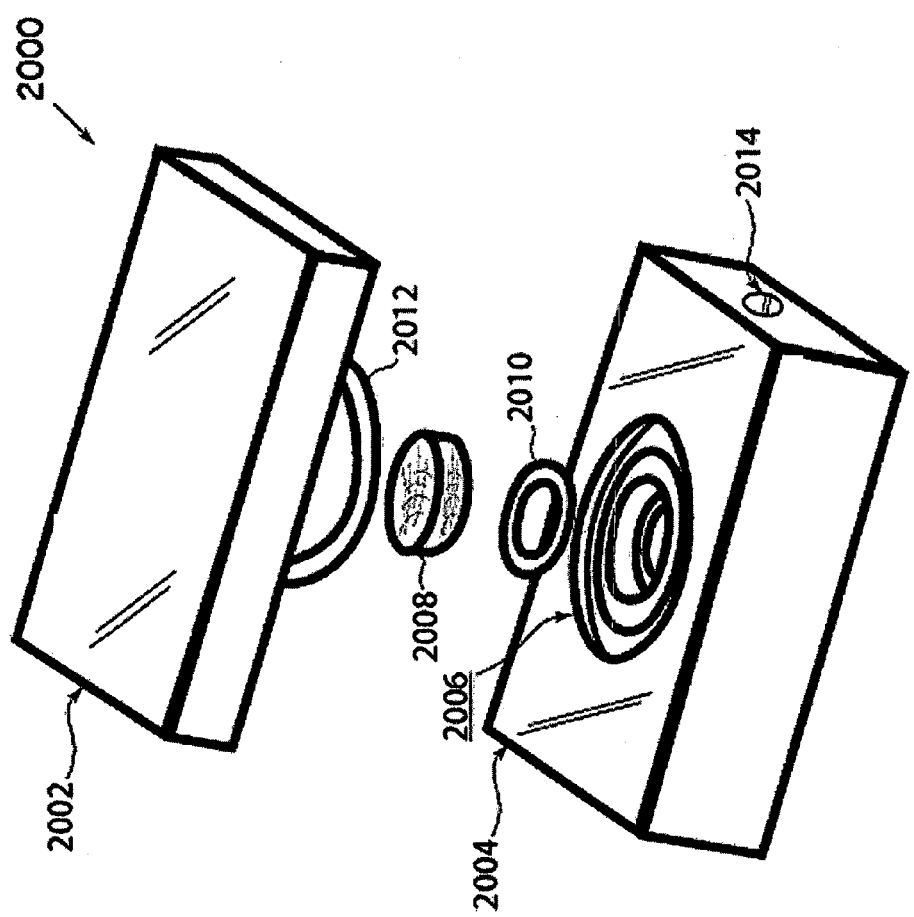
Figure 2B:
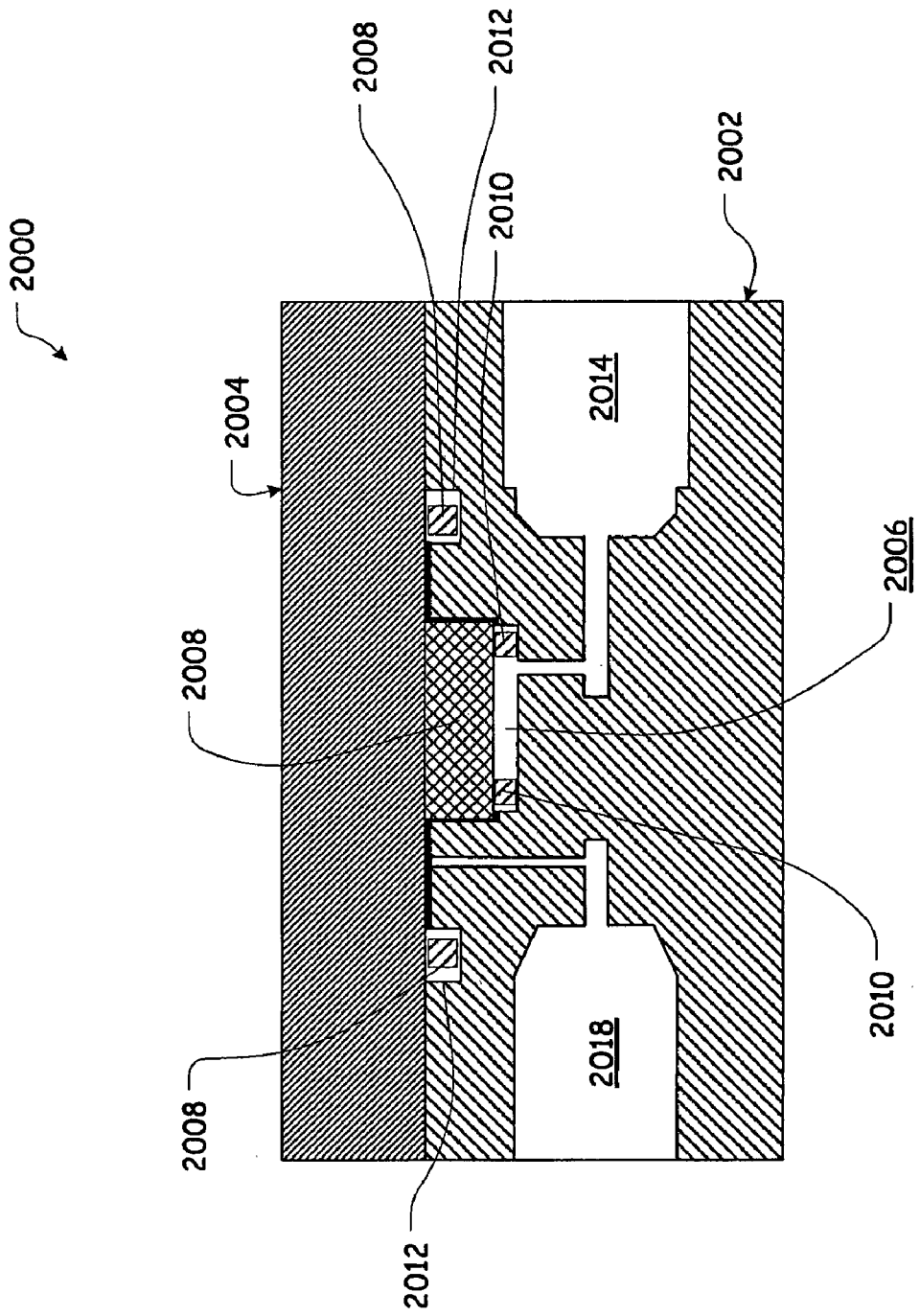
Figure 6:
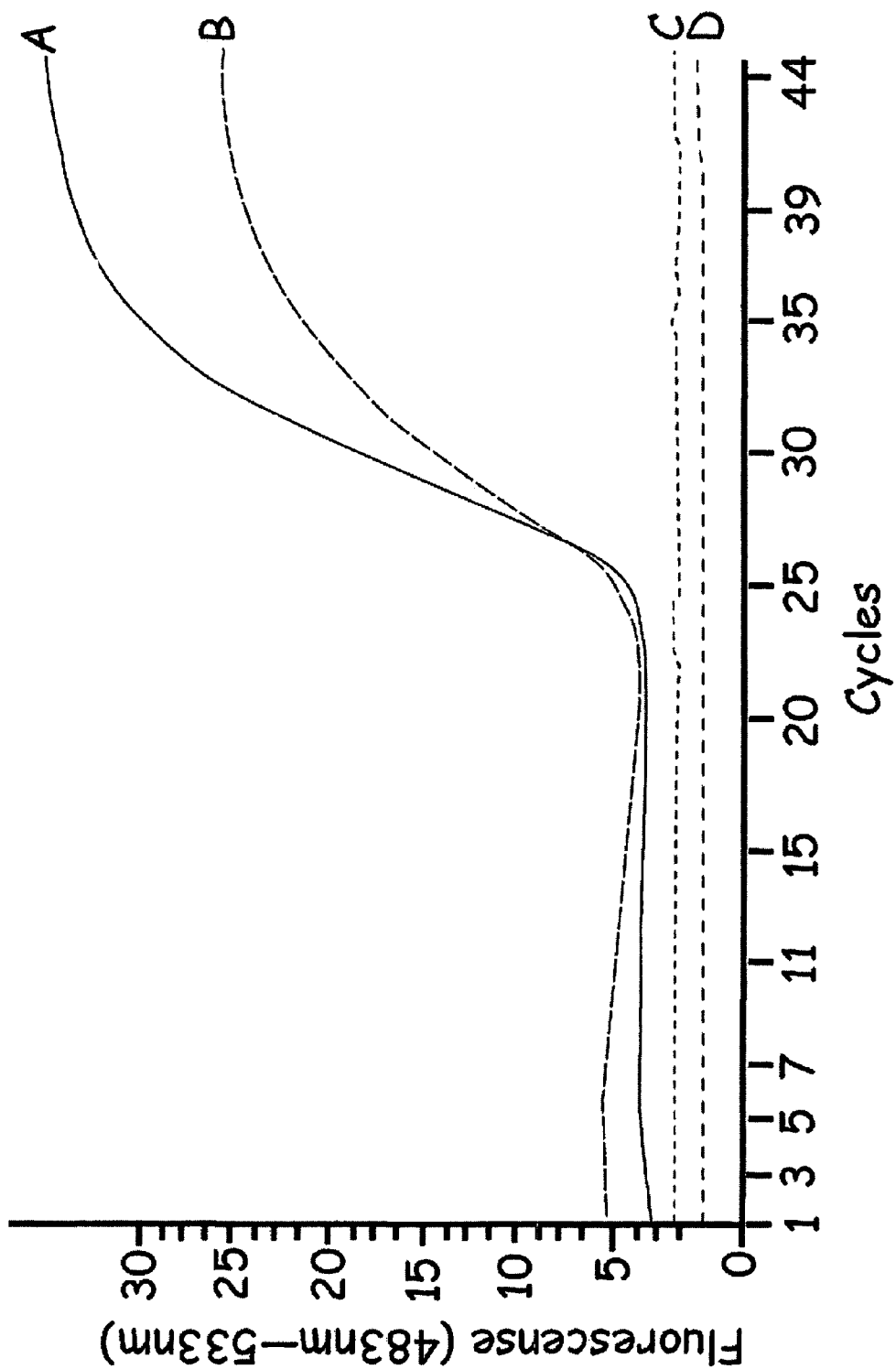

FIG. 6 is graph illustrating the improved performance characteristics of devices in accordance with the present invention as shown in FIGS. 2A and 2B as demonstrated by measuring fluorescence of a sample material (100 μL of *Bacillus anthracis* cells in whole blood at a concentration of $1\times10^5$ cells/mL) as a function of PCR cycles. The solid trace (A) shows the result for samples treated in accordance with the present invention; the dashed trace (B) shows sample treated using a device available commercially from Qiagen; dashed traces (C) and (D) are unprocessed sample and negative control.

FIG. 7 is graph illustrating the improved performance characteristics of devices in accordance with the present invention as shown in FIG. 3 as demonstrated by measuring fluorescence of a sample material (500 μL of *Bacillus anthracis* cells in sputum at a concentration of $1\times10^4$ cells/mL) as a function of PCR cycles. The solid trace (A) shows the result for samples treated in accordance with the present invention; the dashed trace (B) shows unprocessed sample; dashed trace (C) is negative control.

4 DESCRIPTION OF SOME EMBODIMENTS OF THE INVENTION

The present invention provides methods and devices for at least partially purifying nucleic acids from mixtures of such in combination with other substances, such as proteins, small molecules, cell membrane fragments, and the like.

As used herein, "nucleic acids" refers to individual nucleic acids and polymeric chains of nucleic acids, including DNA and RNA, whether naturally occurring or artificially synthesized (including analogs thereof), or modifications thereof, especially those modifications know to occur in nature, having any length. Examples of nucleic acid lengths that are in accord with the present invention include, without limitation, lengths suitable for PCR products (e.g., about 50 base pairs (bp)) and human genomic DNA (e.g., on an order from about kilobase pairs (Kb) to gigabase pairs (Gb)). Thus, it will be appreciated that the term "nucleic acid" encompasses single nucleic acids as well as stretches of nucleotides, nucleosides, natural or artificial, and combinations thereof, in small fragments, e.g., expressed sequence tags or genetic fragments, as well as larger chains as exemplified by genomic material including individual genes and even whole chromosomes. In more specific embodiments, the nucleic acids are from a pathogen, such as bacteria or a virus. Such pathogens include those harmful to humans and animals. Of the former, in some embodiments, the pathogen is one that used as a biological weapon, including naturally occurring pathogens that have been weaponized. In some embodiments, the nucleic acids comprise microbial DNA. In one embodiment of the invention, the microbial DNA is from *Bacillus anthracis*. In other embodiments, the nucleic acids come from humans or animals. In some embodiments, the nucleic acids comprise human genomic DNA.

In a first aspect, the present invention provides methods for isolating nucleic acids from a mixture containing such nucleic acids and extraneous matter. In some embodiments, the methods of the invention comprise passing the mixture through a hollow chamber having an inlet and an outlet; wherein said inlet and outlet are the same and disposed therein at least one porous filter, under conditions effective to separate substantially the nucleic acids from the extraneous matter. As used herein "extraneous matter" refers to all materials that are distinct from the nucleic acids in the sample. Examples of such extraneous materials include, but are not limited to, proteins, starches, lipids, metal ions, and larger cellular structures such as membrane fragments. The phrase "separate substantially" as used herein refers to separations that, in some embodiments, provide the nucleic acids in at least 30% purity with respect to the extraneous materials, in more specific embodiments provide the nucleic acids in at least 50% purity with respect to the extraneous materials, in still more specific embodiments provide the nucleic acids in at least 70% purity with respect to the extraneous materials, in yet more specific embodiments provide the nucleic acids in at least 95% purity with respect to the extraneous materials, and in still yet more specific embodiments, provide the nucleic acids in at least 99% purity with respect to the extraneous materials.

In the various embodiments of the invention described herein, the glass frit is made from standard materials using standard methods as known to persons having ordinary skill in the art or available commercially as described below. In some embodiments, the glass frit has a thickness substantially between about one millimeter and about 20 millimeters, more specifically between about two millimeters and about five millimeters, and still more specifically between about two millimeters and about three millimeters. Exemplary glass frit pore sizes suitable for use with the present invention, including the various embodiments described herein, are between about 2 microns and about 200 microns. In more specific embodiments, the pore size is between about 150 microns and about 200 microns. In other more specific embodiments, the pore size is between about 2 microns and about 100 microns, and still more specifically between about 40 microns and about 75 microns. Other embodiments include those for which the pore size is between about 2 microns and about 20 microns. For applications involving microbial DNA, a glass frit size of between about 10 microns and about 15 microns is suitable. Larger frit pore sizes can be used for human genomic applications. Suitable glass frits are composed of sintered glass and are typically used in chemistry glassware and are available commercially from Robu (Germany). The choice and manufacture of such glass frits will be understood by persons having ordinary skill in the art.

In other embodiments, the glass frit is replaced or used in conjunction with a porous filter. As used herein, "porous filter" refers to any material that allows selective passage of at least one substance contained in a liquid. More specifically, "porous filter" refers to those materials capable of substantially removing nucleic acids from a liquid containing such nucleic acids. Examples of suitable porous filters include, but are not limited to, filter papers configured to trap nucleic acids (e.g., FTA paper, available from Whatman), glass fibers, glass beads, beads with the Charge Switch Technology coating, available from Invitrogen, aluminum oxide filters and porous monolithic polymers. Such materials and products are familiar to those having ordinary skill in the art. In some embodiments, the porous filter is a glass fit. In further embodiment the glass frit is a sintered glass frit. Other suitable materials for providing the filtering function of the glass fit or sintered glass fit are silicone and XTRABIND (Xtrana, Inc., Broomfield, Colo.). The configuration of such materials to perform the filtering functions of the present invention will be apparent to persons having ordinary skill in the art.

Figure 1:
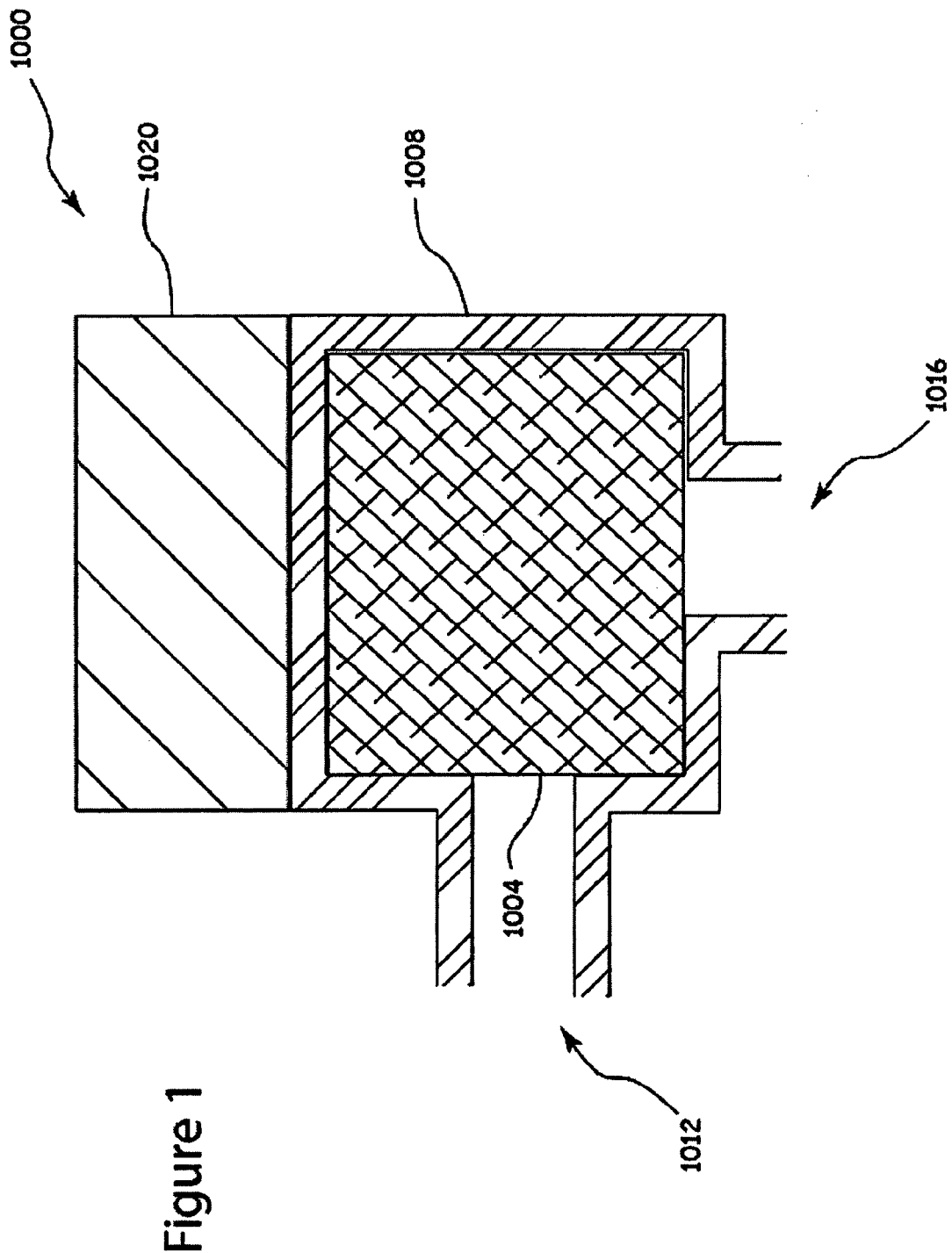

In one embodiment, the above-described glass fit is packaged into a frit holder or fluidic module. One exemplary embodiment of such a holder or module is shown in cut-away view at 1000 in FIG. 1. There, a glass frit as just described above (1004) in placed inside a housing (1008). The housing includes an inlet (1012) into which fluidic mixture including nucleic acids of interest enter the housing and interact with the glass frit as described herein to produce a first-filtered mixture which passes through an outlet of the housing (1016). After exiting the filter holder or module, the first-filtered mixture can proceed to other chambers in fluidic contact with the outlet, such as described below, or to a collector. An optional heater, shown at 1020, is included in some embodiments. The design and manufacture of such devices will be understood by those having ordinary skill in the art.

A second embodiment of this aspect of the invention is shown in FIGS. 2A and 2B. The design and fabrication of such devices are known to those having ordinary skill in the art. FIG. 2A shows an exploded view of one embodiment of a fit holder (2000), which includes an upper housing body (2002) and a lower housing body (2004). The lower housing body includes a recess (2006), described in greater detail in FIG. 2B, into which is disposed one or more glass frits (2008) which are described above. The glass frit is seated in the housing bodies using gaskets (2010, 2012). The lower housing body (2004) also includes an inlet (not shown) through which materials containing nucleic acids to be separated are introduced to glass frit, and outlet (2014) from which waste material and the purified nucleic acids exit the filter module. FIG. 2B shows a cut-away view of the frit housing (2000). There, in addition to the elements just described, the inlet (2018) is shown, along with channels for directing the flow of material through the glass frit and outlet.

In another aspect, the present invention provides a device for isolating nucleic acids from a mixture containing such nucleic acids and extraneous matter. One embodiment of such a filter in accordance with the present invention is shown at 3000 in FIG. 3. There, a hollow chamber (3004) having a first opening (3008) and a second opening (3012) through which a mixture comprising nucleic acids is passed and an outlet from which an at least partially resolved mixture exits. Between the inlet and outlet is a glass frit (3018) as described above that extends axially through at least a portion of the interior volume of the hollow chamber, the extent to which is shown at 3016. In some embodiments, more than one such fit is used. In still other embodiments, at least one of the glass fits is made of sintered glass. The design and fabrication of such devices are known to those having ordinary skill in the art.

In some more specific embodiments, one end of the hollow chamber has a frustaconical shape the chamber is dimensioned to fit on the end of a pipetting instrument, e.g., as a pipet tip, so that materials are first taken up though the second opening, pass through the glass frit, are filtered and then retained in the portion of the chamber above the frit. In some embodiments, the sample retained in the portion of the chamber above the frit is passed back through the frit through the second opening (3012).

In another embodiment, the above-described pipet tip is combined with a heating device that is configured to heat the frit to facilitate separation of the nucleic acids from the mixture. In more specific embodiments, the heater is dimensioned to fit within the pipet tip. The design and fabrication of such devices are known to those having ordinary skill in the art.

In still another embodiment, the pipet tip is coupled with an electronic pipettor or robotic pipetting workstation to control the flow rate through the frit. In some embodiments, the electronic pipettor is a hand-held device. The design, fabrication, and operation of such devices are known to those having ordinary skill in the art.

In some embodiments of the present invention, two or more porous filters are used in combination. In a more specific embodiment, each layer has a different pore size. Without wishing to be bound to any particular theory of action, larger porous filter pore sizes trap larger particles, and so can serve as a prefilter. For example, a 40 micron-60 micron porous filter could be used in tandem with a 10 micron-15 micron porous filter to deplete human genomic DNA from a sample (e.g., blood) to isolate microbial DNA. Removing the abundant human DNA with the 40 micron-60 micron porous filter allows better binding of the low copy microbial DNA to the 10 micron-15 micron porous filter and more robust analysis, since the human genomic DNA will not be present in concentrations large enough to interfere significantly (e.g., by whole genome amplification). The porous filter can be in a pipet tip as described above, having a thickness and diameter of about five millimeters (mm) each. In some embodiments, two or more of the porous filters are fused together to form a substantially monolithic structure. The design, fabrication, and operation of such devices are known to those having ordinary skill in the art.

In more specific embodiments in which the filter is disposed with a pipet tip, the glass frit(s) having larger pore sizes are disposed closer to the pipet tip inlet. Again not wishing to be bound to any particular theory of action, but those persons having ordinary skill in the art will appreciate that arranging the larger pore sized filter nearer the pipet tip inlet can provide a more uniform distribution of nucleic acid binding within the frit. By way of comparison, persons having ordinary skill in the art will expect that otherwise the nucleic acids will tend to bind to the frit at the area closest to the pipet tip opening, since the nucleic acids are more likely to make initial contact just as the nucleic acids enter the frit.

In yet another aspect, the present invention provides a microfluidic device for analyzing nucleic acids in accordance with the present invention. One embodiment of such a microfluidic device is show in FIG. 4 at 4000. A frit holder (4002) as described herein is provided. Upstream, the frit holder in fluidic communication with a source of elution buffer (4004), a guanidine hydrochloride (Gu) reservoir (4006) and Gu mixing tower (4008), the flow from which Gu and Gu mixing tower are controlled by a valve (4010). The Gu mixing tower is further in fluidic communication with an ethanol-air source (4012). Those persons having ordinary skill in the art will realize that chaotropes other than Gu can be used with the present invention. In addition are a bead beater (4014) that is in fluidic communication with a sample collection tower (4016), which is in turn in fluidic communication with inlet check value (4018), and an electrical contact (4020). The output from these elements is controlled by valve 4022.

Figure 4:
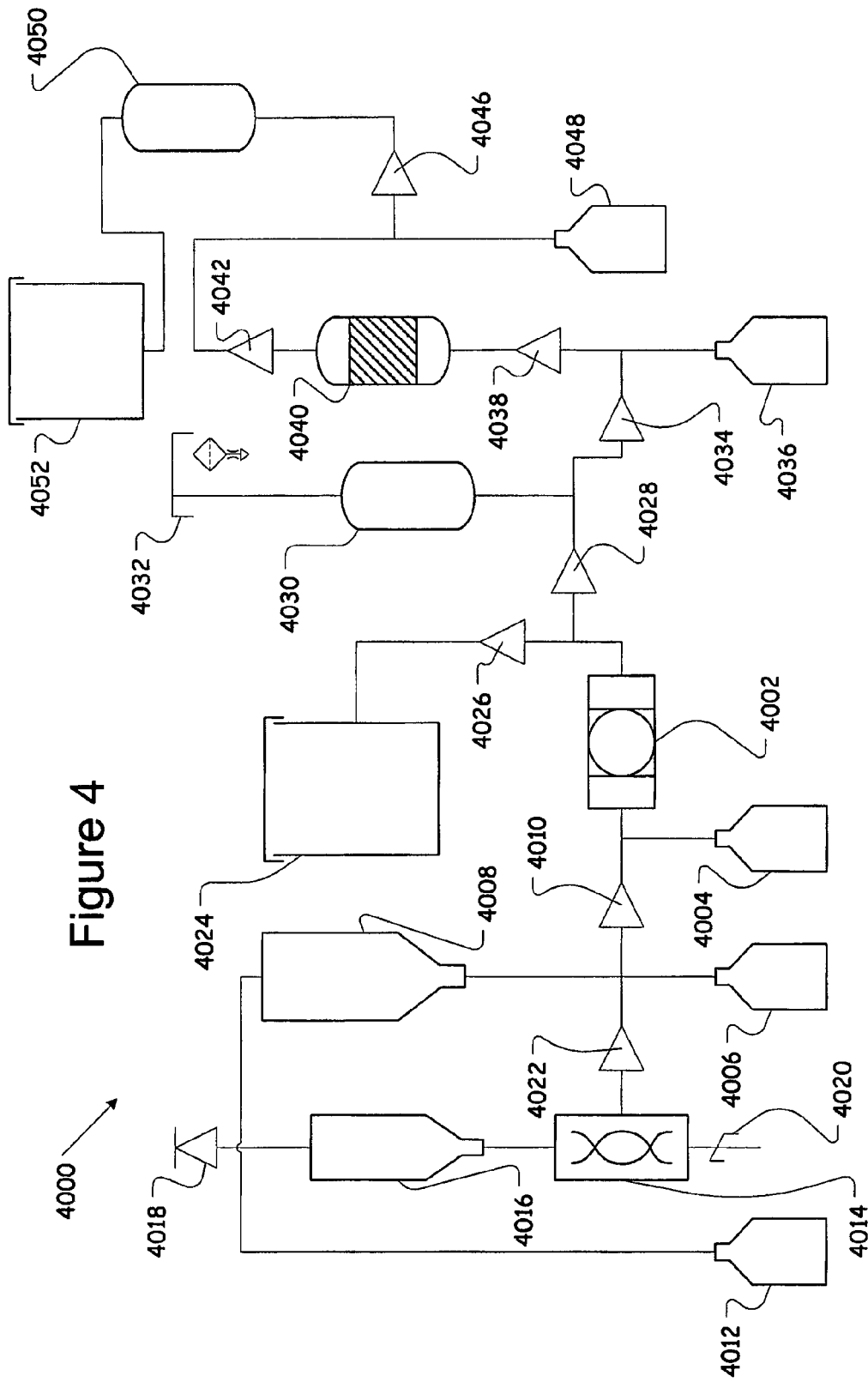
FIG. 4 is a schematic illustration of a microarray device in accordance with the present invention.

With continuing reference to FIG. 4, downstream of frit holder (4002) is a waste tank (4024), the flow to which is controlled by a valve (4026). Downstream flow from the fit holder is also controlled by a second valve (4028), which controls flow to an elution tower (4030) and a check valve (4032) along a first branch; and to another valve (4034) along a second branch of the flow path Continuing downstream from valve 4034, are one or more reservoirs of PCR reagents (4036) and a valve (4038) which leads to a PCR chamber (4040). Downstream of the PCR chamber is a valve (4042), which, along with valve 4046, controls flow from the PCR chamber to a microarray chamber (4048) that is also in fluidic communication with hybridization and wash buffer reservoir (4048) and a waste container (4052). The design and fabrication of such devices are known to those having ordinary skill in the art.

Figure 5:
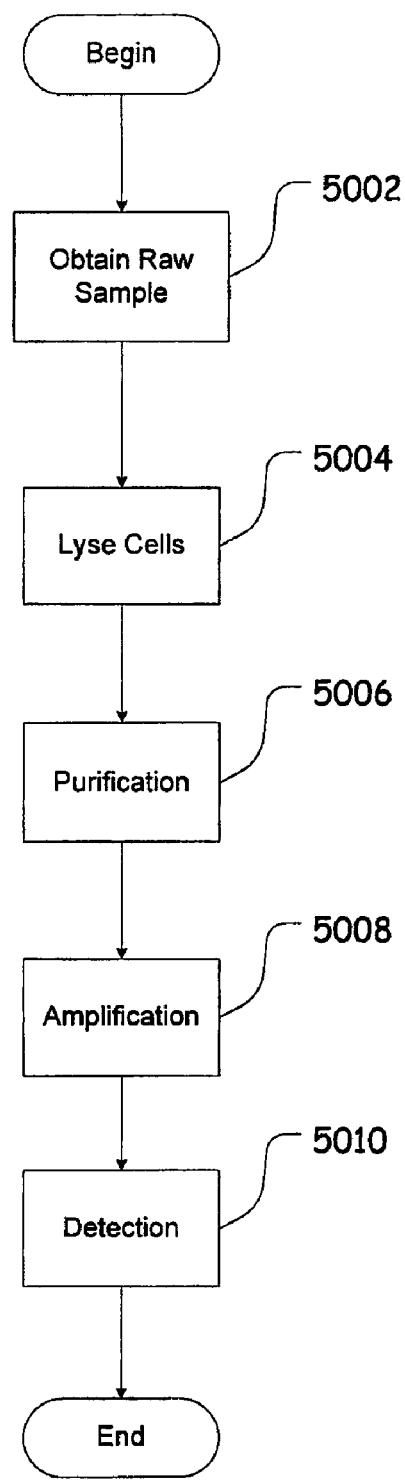
FIG. 5 is a flowchart of a process for purifying and identifying nucleic acids in accordance with the present invention.

The operation of the device described with respect to FIG. 4 is illustrated by the flowchart shown in FIG. 5 at 5000. After obtaining the raw sample (5002), e.g., a sputum sample that contains cells of interest, the cells are lysed (5004) using bead beater 4014, and the mixture passed for purification of the nucleic acids (5006) through the frit 4002 for amplification (5008) by PCR chamber 4040 and detection (5010) by the microarray chamber 4050.

Without being bound to any particular theory or action, the present invention meets the needs described above by implementing a rigid, self-supporting fit structure that is relatively thick for high binding capacity, contains relatively large porosities for low fluid impedance, faster flow rates, and higher tolerance to particles in clinical and environmental samples, and consists of no loose material (e.g. silica gel, diatomaceous earth, glass beads) and no flimsy, delicate materials (e.g. fiber filters, membrane filters, silicon microstructures) for rugged operation and packaging and simplified manufacturing.

5 EXAMPLES

The following Examples are provided to illustrate certain aspects of the present invention and to aid those of skill in the art in the art in practicing the invention. These Examples are in no way to be considered to limit the scope of the invention in any manner.

5.1 Protocol for Using a Device of the Invention

Referring to FIGS. 2A and 2B, a protocol for practicing purification and detection in accordance with the present invention is provided below.

1. Insert a glass frit into holder (one of four different porosities: Fine, Medium. Coarse, and Extra Coarse). Tighten the housing.
2. Mix 500 μL of a sample ($10^4$ copies/mL) with 500 μL of 6M guanidine, pH 6.5.
3. Pass mixture (1 mL) through frit at a flow rate of 100 μL/min using a 1 mL syringe. Pass air manually through frit to purge sample using a 5 mL syringe.
4. Pass 1 mL of 70% ethanol (EtOH) to wash bound nucleic acid using a 1 mL syringe at rate of 1 mL/min Pass air through the frit manually to purge EtOH using a 5 mL syringe.
5. Carefully pass an elution buffer (10 mM Tris, pH 8.0) using 1 mL syringe at 100 μl/min into the frit holder until buffer can be first seen in the outlet tubing.
6. Place heat block under the frit holder and heat at 70° C. for 3 min.
7. After 3 minutes continue to pass elution buffer through frit holder. Collect the fractions (50 μL-100 μL) for PCR analysis.
8. Flush the frit holder with 1 mL of 10% bleach (bleach dilution no more than one week old), 5 mL of 10 mM Tris-HCl (pH 8.0), and 5 mL of water. Replace the frit.

5.2 Second Protocol for Practicing the Invention

Figure 3:
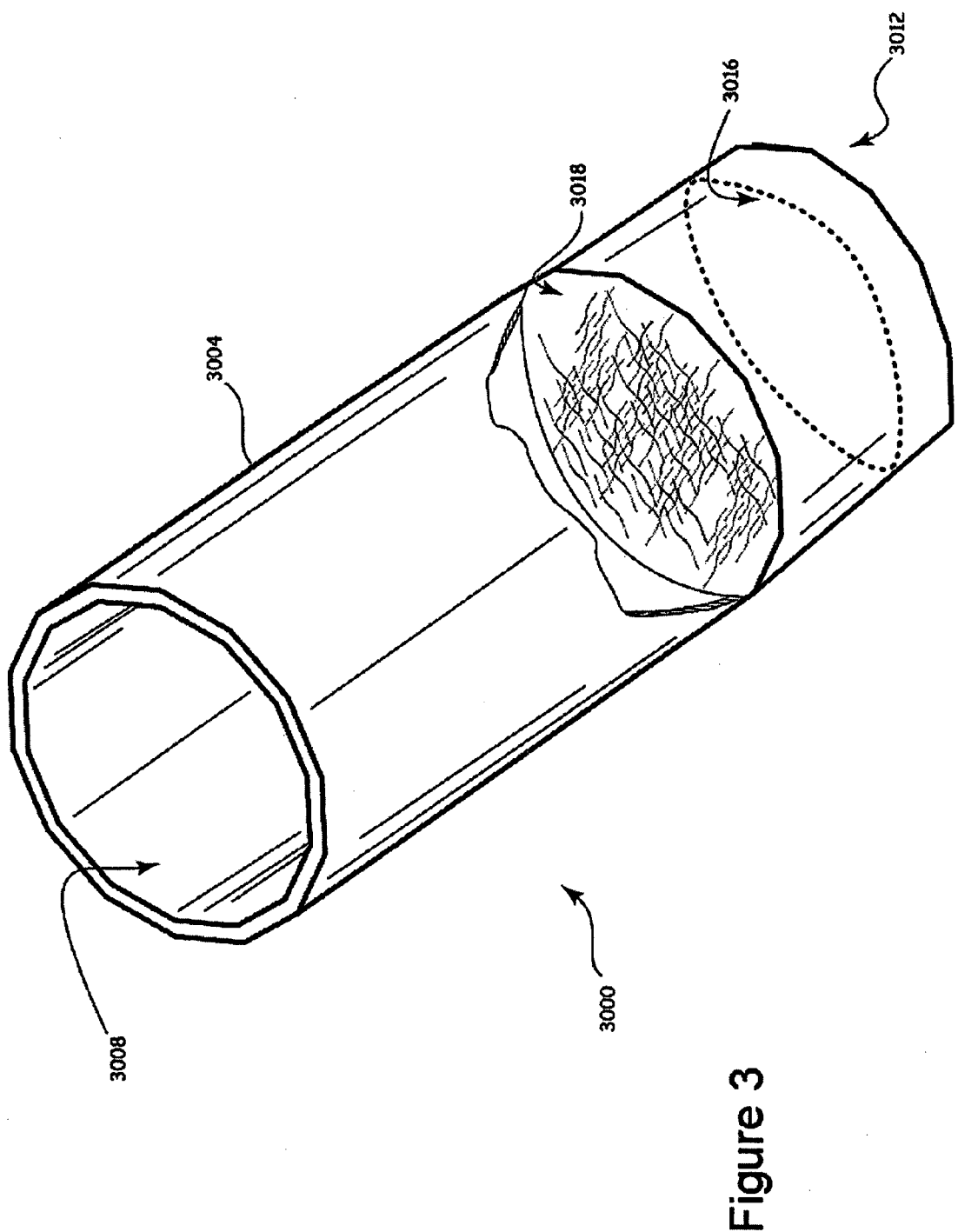
FIG. 3 is a schematic illustration of a glass frit device ("a hollow chamber") for purifying nucleic acids in accordance with the present invention.

Referring to FIG. 3, a protocol for practicing purification and detection in accordance with the present invention is provided below.

1. Add 500 μL of sample to 500 μL of 6M guanidine in Vial A. Vortex to mix.
2. Attach a 1.2 mL pipet tip with an embedded frit to an electronic pipettor (Gilson Concept).
3. Set electronic pipettor to speed 1 (slowest speed). Aspirate the 1 mL of sample mixture in Vial A. Allow the sample mixture bolus to completely pass through the frit. The sample mixture bolus will establish itself immediately on top of the frit.
4. Dispense the sample back into Vial A. The sample mixture bolus will completely expel back into the vial.
5. Repeat steps 3 and 4 four times.

6. Set electronic pipettor to speed 5 (fastest speed). Aspirate and dispense 1 mL of 70% ethanol in Vial B to wash bound nucleic acids on frit. Repeat four times.

7. Remove traces of ethanol by positioning tip above the ethanol solution. Aspirate and dispense air five times to dry the fit.

8. Place Vial C containing 100 µl of 10 mM Tris-HCl (pH 8.0) into a heat block set at 70° C. Let heat for 5 minutes.

9. Set the electronic pipettor to speed 1. Aspirate the elution buffer and dispense back into Vial C five times to remove nucleic acids from the frit.

5.3 Demonstration of Superior Results From the Invention

Figure 7:
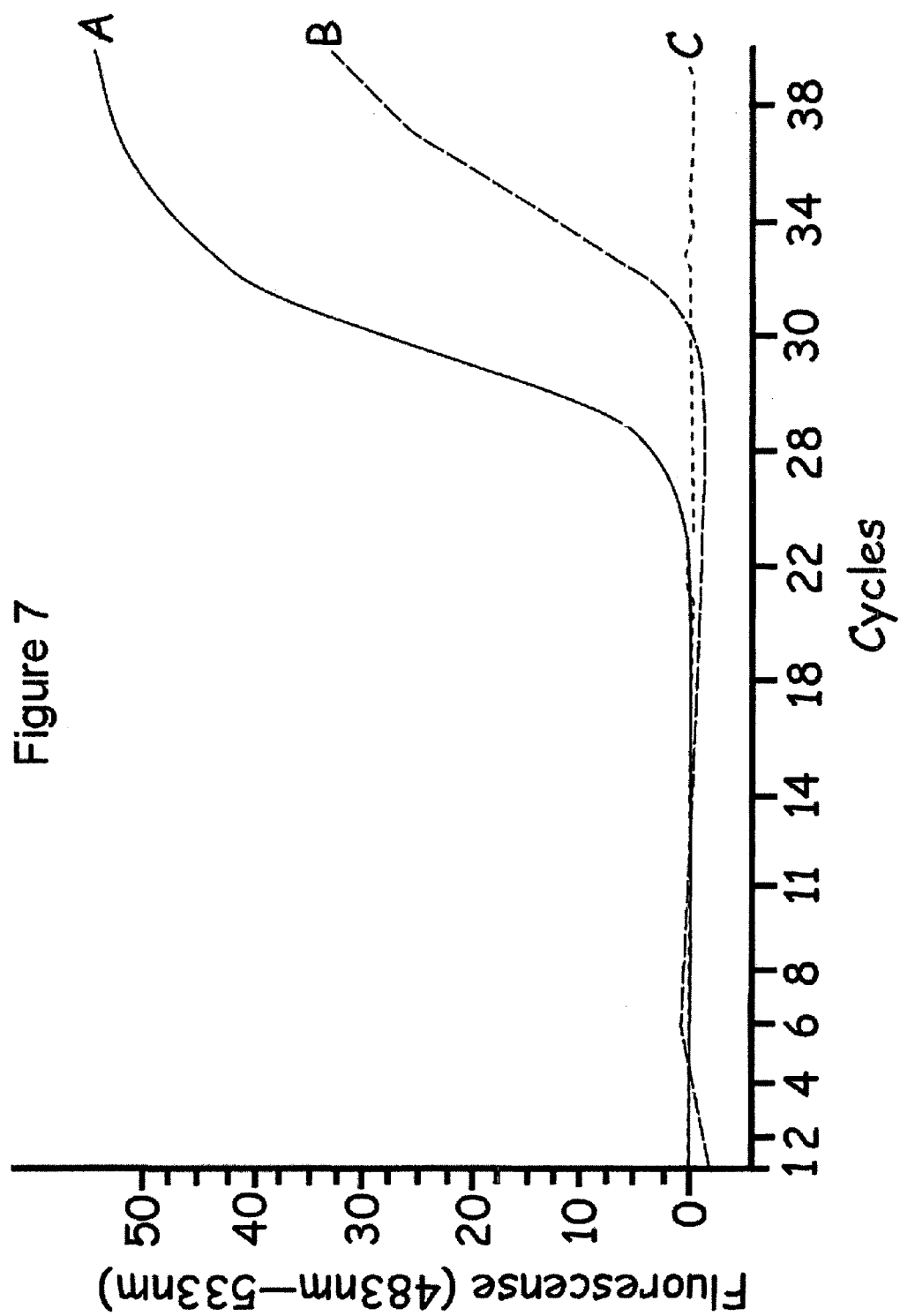

The results of two experiment using such protocols are show in FIGS. 6 and 7, where samples of *Bacillus anthracis* (Ba) in whole blood and sputum were treated using the materials and methods of the invention.

In FIG. 6, the sample treated using a method and device (FIGS. 2A and 2B) of the invention (trace A) outperformed a sample treated using a device available commercially from Qiagen (trace B). Traces C and D are the unprocessed input sample and negative control, respectively. In the experiment, 100 µL of *Bacillus anthracis* cells at $10^5$/mL in whole blood was input, either through a medium (10-15 µm pore size) frit as described herein or into a Qiagen device, and elutions of about 50 µL were collected and analyzed using PCR. As the Figure illustrates, after about 25 cycles of PCR amplification, the sample treated using the materials and methods of the invention clearly and significantly outperform the results from the sample treated using the prior art device.

FIG. 7 illustrates the result of another experiment using such a method and device (FIG. 3), where a sample of *Bacillus anthracis* cells in sputum was treated using the materials and methods of the invention. The sample treated using the method and device of the invention (trace A) outperformed an unprocessed sample (trace B). Trace C is a negative control. In the experiment, 500 µL of *Bacillus anthracis* cells at $10^4$/mL in sputum was input through a medium frit as described herein, and an elution of about 100 µL was collected and analyzed using quantitative, real-time PCR. As the Figure illustrates, after about 27 cycles of PCR amplification, the sample treated using the material and method of the invention clearly and significantly outperform the results from unprocessed sample.

The above-described methods and devices were used successfully to identify DNA and/or RNA from a variety of organisms listed in Table 1 that were spiked into a variety of matrices (i.e., sample types) listed in Table 2.

TABLE 1

Viral Equine Encephalitis (VEE)
Vaccinia virus
*Y. pestis*
*B. anthracis*
Adenovirus
*S. pyogenes*
*C. pneumoniae*
Influenza A
Influenza B
Mixture of Adenovirus + *S. pyogenes*
Mixture of Flu A and Adenovirus The following materials were analyzed successfully using the methods and devices of the invention:

TABLE 2

Water/TE (10 mM Tris-HCl, 1.0 mM EDTA buffer)
Swab extracts
Sputum
Nasal Wash
Whole Blood

6 CONCLUSION

The present invention offers several advantages over the prior art: 1) a simplified method and device requiring no centrifugation or high pressure to move fluids, 2) a modular device for fluidic integration into a complete analytical system, 3) large pore sizes to process complex samples while maintaining low fluid resistance; 4) high extraction and elution efficiencies since fluids can be moved from both directions; 5) rigidity that eliminates the need for additional support structures, and 6) durability that allows reusing the device for sequential samples. Although various specific embodiments and examples have been described herein, those having ordinary skill in the art will understand that many different implementations of the invention can be achieved without departing from the spirit or scope of this disclosure. For example, other materials with nucleic acid affinity could be used for the glass frit or the glass fit can be modified to better attract nucleic acids and nucleic acids without using a chaotropic salt such as guanidine. Glass fits can contain immobilized antibodies to extract microbes and toxins. Still other variations will be clear to those having ordinary skill in the art.

7 BIBLIOGRAPHY

The following references are incorporated herein by reference in their entirety and for all purposes.

Beach, R. A., Strittmatter, R. P., et al. (2007). Integrated Micropump Analysis Chip and Method of Making the Same U.S. Pat. No. 7,189,358.

Colpan, M. (2001). Process and device for the Isolation of Cell Components, Such as Nucleic Acids, from Natural Sources U.S. Pat. No. 6,274,371.

Deshmukh, A. J. (2006). Method and Automated Fluidic System for Detecting Protein in Biological Sample U.S. Pat. No. 6,989,130.

Kalra, K. L., Pawlak, K., et al. (1990). Immunoassay Test Device and Method U.S. Pat. No. 4,912,034.

Knollenberg, B. A., Rodier, D., et al. (2007). Molecular Contamination Monitoring System and Method U.S. Pat. No. 7,208,123.

McCormack, R. M. (1990). Process for Purifying Nucleic Acids U.S. Pat. No. 4,923,978.

Terry, B. R., Scudder, K. M., et al. (2004). Method and Apparatus for High Density Format Screening for Bioactive Molecules. U.S. Pat. No. 6,790,652.

Tittgen, J. (2004). Chromatography Material and a Method Using the Same U.S. Pat. No. 6,800,752.

Wick, C. H. (2007). Method and System for Detecting and Recording Submicron Sized Particles. U.S. Pat. No. 7,250,138.

What is claimed:

1. A method for isolating nucleic acids from a mixture containing such nucleic acids and extraneous matter, comprising:

flowing said mixture through the interior volume of a hollow chamber; said hollow chamber having disposed therein at least one sintered glass frit that binds to said nucleic acids, said glass frit being arranged within said hollow chamber such that said mixture flows through said glass frit, under conditions effective to separate substantially said nucleic acids from said extraneous matter, wherein said glass frit having a pore size of between about 2 microns and about 20 microns, wherein said glass frit is a rigid, self-supporting frit with a thickness of about 1-20 mm, and wherein said glass frit is not modified with a material with nucleic acid affinity.

2. The method of claim 1, wherein said nucleic acids comprise microbial DNA and RNA.

3. The method of claim 1, wherein said nucleic acids comprise human genomic DNA and RNA.

4. The method of claim 1, wherein said flowing said mixture through a glass frit produces a first-filtered mixture and said method further comprises flowing said first-filtered mixture through a second glass frit under conditions effective to separate said nucleic acids from said first-filtered mixture.

5. A method for isolating nucleic acids from a mixture containing such nucleic acids and extraneous matter, comprising:

flowing said mixture through the interior volume of a hollow chamber; said hollow chamber having disposed therein at least one sintered glass frit that binds to said nucleic acids, wherein said glass frit is a rigid, self-supporting frit and wherein said glass flit has a pore size between about 2 microns and about 220 microns, and said glass frit being arranged within said hollow chamber such that said mixture flows through said glass frit, wherein said flowing includes flowing said mixture across said glass frit in a first direction and then flowing said mixture across said glass frit in a direction opposite said first direction, such that said mixture passes through said glass frit at least twice, under conditions effective to separate substantially said nucleic acids from said extraneous matter.

6. The method of claim 5, wherein said glass frit has a pore size between about 150 microns and about 200 microns.

7. The method of claim 5, wherein said glass fit has a pore size between about 2 microns and about 100 microns.

8. The method of claim 5, wherein said glass frit has a pore size between about 40 microns and about 75 microns.

9. The method of claim 5, wherein said glass frit has a pore size between about 2 microns and about 20 microns.

10. A method for isolating nucleic acids from a sample, comprising:

lysing said sample to form a sample lysate;

flowing said sample lysate through the interior volume of a hollow chamber; said hollow chamber having disposed therein a sintered glass frit that binds to said nucleic acids, wherein said glass frit is a rigid, self-supporting frit and wherein said glass flit has a pore size between about 2 microns and about 220 microns, wherein said glass frit is not modified with a material with nucleic acid affinity and wherein nucleic acids in said sample lysate bind to said glass frit;

eluting bound nucleic acids from said glass frit.

11. The method of claim 10, wherein said nucleic acids comprise microbial DNA and RNA.

12. The method of claim 10, wherein said nucleic acids comprise human genomic DNA and RNA.

13. The method of claim 10, wherein said glass frit has a pore size between about 150 microns and about 200 microns.

14. The method of claim 10, wherein said glass fit has a pore size between about 2 microns and about 100 microns.

15. The method of claim 10, wherein said glass frit has a pore size between about 40 microns and about 75 microns.

16. The method of claim 10, wherein said glass fit has a pore size between about 2 microns and about 20 microns.

* * * * *